United States Patent [19]

Ewing et al.

[11] Patent Number: 5,621,522
[45] Date of Patent: Apr. 15, 1997

[54] FIBER OPTIC PROBE FOR DETERMINATION OF TRACE LEVELS OF ORGANIC POLLUTANTS USING RAMAN SPECTROSCOPY

[75] Inventors: Kenneth J. Ewing, Bowie, Md.; Thomas Bilodeau; Gregory Nau, both of Alexandria, Va.; Ishwar Aggarwal, Fairfax Station, Va.

[73] Assignee: The United States of America as represented by the Secretary of the Navy, Washington, D.C.

[21] Appl. No.: 417,164

[22] Filed: Apr. 5, 1995

[51] Int. Cl.⁶ .............................. G01J 3/44; G01N 21/65
[52] U.S. Cl. ................................................. 356/301
[58] Field of Search ............................................. 356/301

[56] References Cited

U.S. PATENT DOCUMENTS 5,255,067  10/1993  Carrabba et al. ................... 356/301
5,400,136   3/1995  Vo-Dinh ............................. 356/301

OTHER PUBLICATIONS

D.S. Ballantine, Jr. et al., *Analytical Chemistry* 58 3058–66 (1986).
R.A. McGill et al., "Choosing Polymer Coatings for Chemical Sensors", *Chemtech* 24 (9) 27–37.
S.D. Schwab et al., "Versatile, Efficient Raman Sampling with Fiber Optics", *Analytical Chemistry* 58 2199–2204 (1984).

*Primary Examiner*—F. L. Evans
*Attorney, Agent, or Firm*—Thomas E. McDonnell; John J. Karasek

[57] ABSTRACT

The present invention is a chemical sensor including a polymer substrate capable of reversible adsorption of an analyte organic compound, a source of Raman excitation radiation, positioned for directing this Raman excitation radiation onto the substrate, thus generating a Raman signal, and a Raman signal detector, positioned for detecting this Raman signal. Another aspect of this invention is the sensing tip of such a sensor, including a polymer substrate capable of reversible adsorption of an analyte organic compound, focusing means for directing excitation radiation onto the polymer substrate to generate a Raman signal from the organic compound, and collection means, for transmitting this Raman signal to a detector. Another aspect of this invention is an array of sensing tips, each using a different polymer substrate selected for selective adsorption of an analyte species, coupled to an excitation radiation source and a detector.

21 Claims, 7 Drawing Sheets

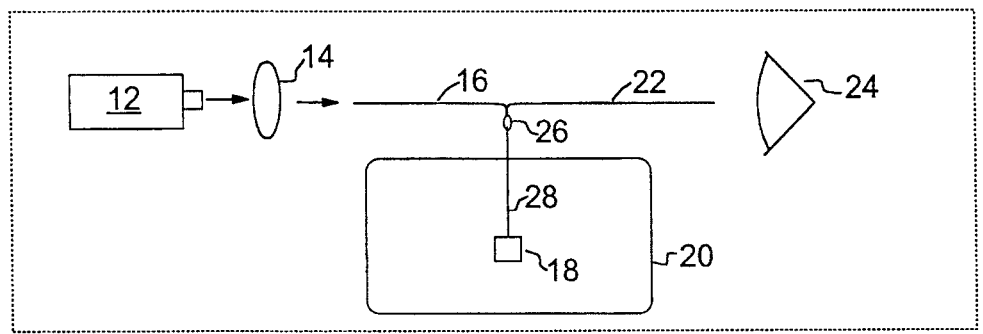
FIG. 1
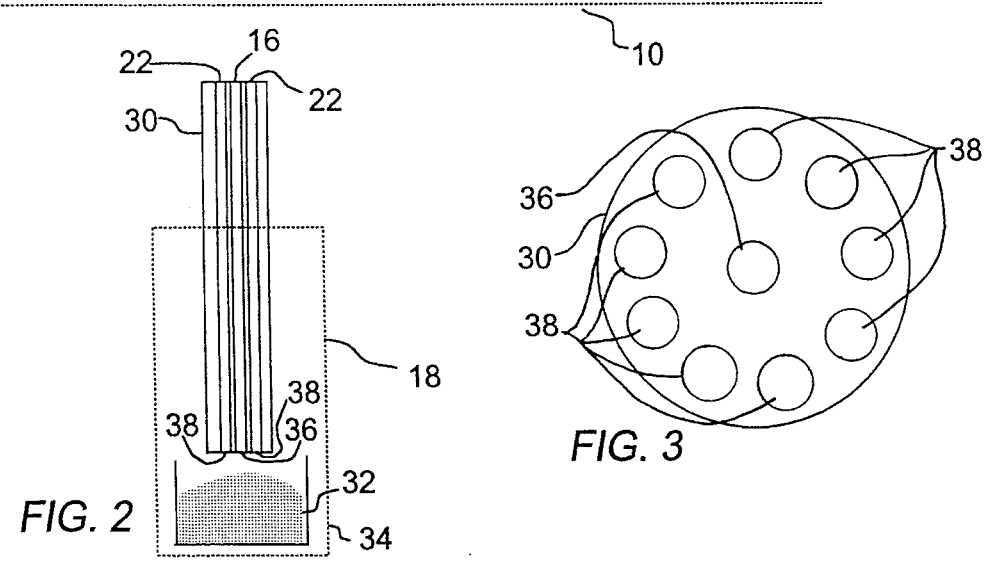
FIG. 2
FIG. 3

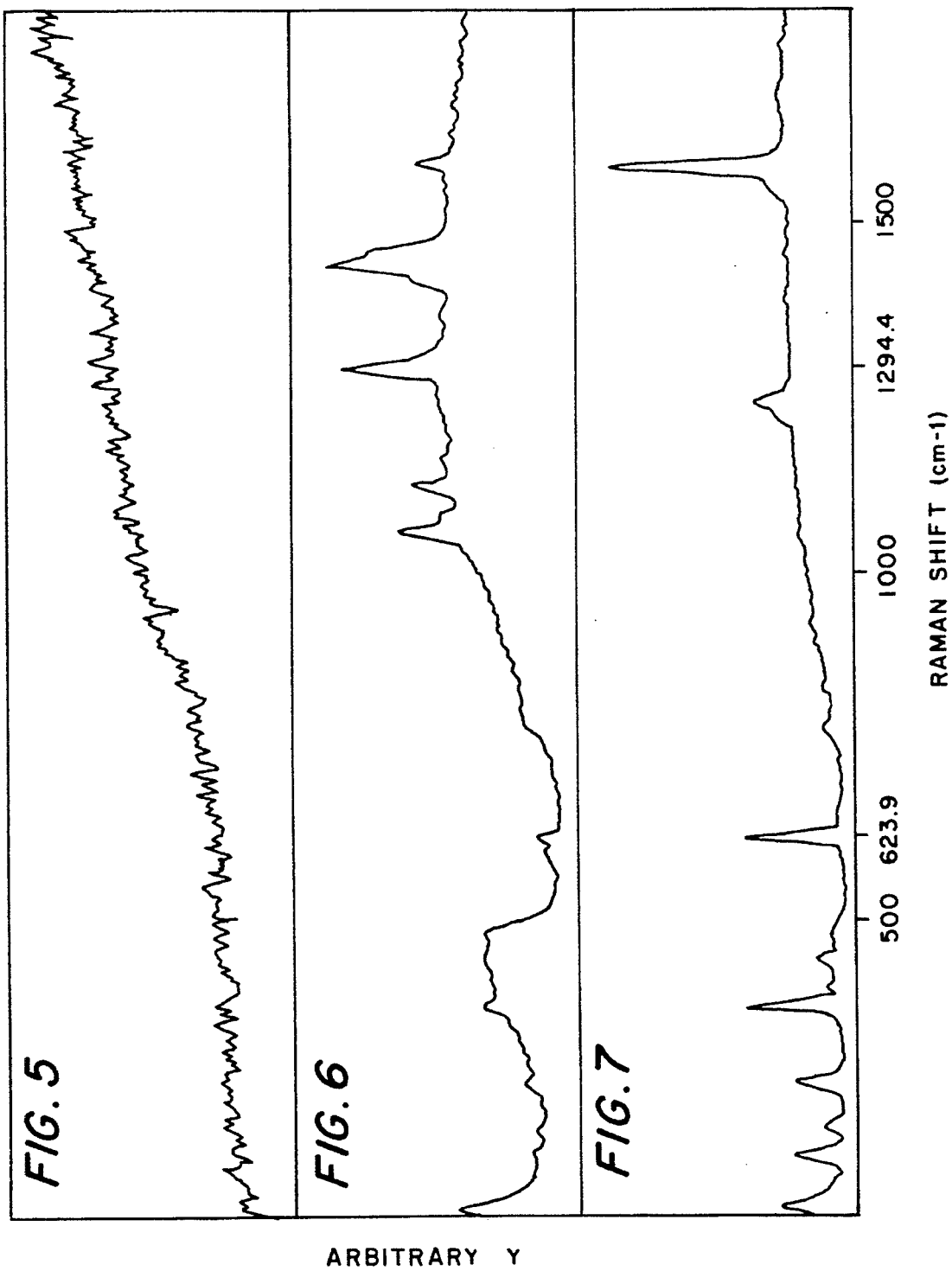

FIBER OPTIC PROBE FOR DETERMINATION OF TRACE LEVELS OF ORGANIC POLLUTANTS USING RAMAN SPECTROSCOPY

BACKGROUND OF THE INVENTION

1. Field of the Invention

This invention relates to the detection of trace levels of organic pollutants using Raman spectroscopy. More particularly, this invention relates to using polymer substrates to preconcentrate analytes to improve the sensitivity of Raman spectroscopy.

2. Description of the Related Art

Many techniques are known for detecting organic compounds in situ in vapor and/or liquid phase. However, all of the available techniques have some shortcomings. One problem common to many analytical techniques is the need to regularly calibrate the sensor using some reference standard. It would be desirable to have a sensor that could be internally calibrated.

Raman spectroscopy is an advantageous technique for detecting organic compounds, due to its high selectivity. A Raman signal can be associated with a unique organic compound. Raman spectroscopy works by laser probe light exciting molecules to higher energy states, often in their vibrational energy bands. As these molecules return to equilibrium, they emit characteristic Raman signal photons. This emitted light can then be analyzed to determine the specie and its amount in the solution.

Unfortunately, Raman spectroscopy has a fairly high lower limit of detection (LLD). One method that has been used as a work-around to this high LLD is surface enhanced Raman spectroscopy, or SERS. SERS improves the LLD by using a substrate with a thin metallic coating that essentially irreversibly adsorbs the analyte, to preconcentrate the analyte. A good review of SERS can be found in Keith T. Carron's dissertation, Surface Enhanced Resonance Raman, Resonance Hyper-Raman, and Hyper-Raman Spectroscopy of Molecules Absorbed to Thin Metal Films, Northwestern University 1985.

SERS has its own drawbacks. This thin metal coating must be prepared with great care to achieve optimal results. SERS is also not generally available: only certain species of organic compounds are amenable to detection using this technique. Also, a SERS sensor substrate generally can be used only once, because the binding between the substrate and the analyte is essentially irreversible.

Resonance Raman spectroscopy is another technique that has been developed to improve the limits of detection. However, Resonance Raman spectroscopy is not suitable for in situ analysis.

Fiber optic infrared spectroscopy provides in situ real time analysis, and is highly selective. However, there are problems with the available optical fibers that transmit infra-red light. These fibers have a limited optical window, particularly with extended fibers. $CCl_4$, for example, cannot be detected with an extended fiber. Trichloroethylene is marginally detectable. These fibers also lose a large fraction of signal during transmission. Currently available IR optical fibers have power losses ranging from 1,000 to 10,000 dB/km. Even assuming a tenfold improvement in the power loss of IR optical fibers, to between 100 and 1,000 dB/km, this would still be much higher than the 0.2 to 10 dB/km power loss that is typical for silica optical fibers. Further, no couplers are currently available for these fibers, making multiplexing problematic.

Gas chromatography is highly selective, is amenable to use with a broad range of analytes, and has an excellent LLD, especially when coupled with mass spectrometry. However, gas chromatography is not an in situ technique, and errors can be introduced by improper sampling.

Another technique that has developed for chemical sensing is surface acoustic wave analysis, or SAW. SAW analysis works by measuring the change in the vibrational frequency of a thin polymer film, as analyte molecules adsorb or desorb from the polymer film. See U.S. patent application Ser. No. 07/970,750, incorporated in its entirety by reference herein. SAW has its own drawbacks, however. It is not very selective, and it does not work in liquid phase analysis.

A consequence of the extensive research that has been done on SAW analysis is that a large number of polymers have been identified as selective adsorbents for particular organic analytes. See generally, D. S. Ballantine, Jr., S. L. Rose, J. W. Grate, H. Wohltjen, *Analytical Chemistry* 58 3058–66 (1986), and references therein, incorporated by reference herein. See also R. A. McGill et al., "Choosing Polymer Coatings for Chemical Sensors, CHEMTECH 24 (9) 27–37, and references therein, incorporated by reference herein. Despite this effort, SAW analysis remains relatively poorly selective. Table I lists a few of these polymers, and the organic species that are selectively adsorbed by them:

TABLE I

| POLYMER | ANALYTE |
|---|---|
| poly(isobutylene) | TCE, chloroform |
| poly(cyanoallyl)-siloxane | methylene chloride |
| poly(phenylether) | benzene |
| fluoropolyol | dimethyl(methylphosphinate) |

SUMMARY OF THE INVENTION

Accordingly, it is an object of this invention to provide a highly selective in situ chemical sensor with a good LLD, general applicability, internal calibration, the ability to work with mixtures of analytes, and the ability to work for both vapor phase and liquid phase analytes.

It is a further object of this invention to provide a reusable chemical sensor.

These and additional objects of the invention are accomplished by the structures and processes hereinafter described.

The present invention is a chemical sensor including a substrate capable of reversible adsorption of an analyte organic compound, a source of Raman excitation radiation, positioned for directing this Raman excitation radiation onto the substrate (typically by the use of an optical fiber), thus generating a Raman signal, and a Raman signal detector, positioned for detecting this Raman signal (typically by the use of one or more optical fibers).

Another aspect of this invention is the sensing tip of such a sensor, including a substrate capable of reversible adsorption of an analyte organic compound, focusing means for directing excitation radiation onto the polymer substrate to generate a Raman signal from the organic compound, and collection means, for transmitting this Raman signal to a detector.

Another aspect of this invention is an array of sensing tips, each using a different polymer substrate selected for selective adsorption of an analyte species, coupled to an excitation radiation source and a detector.

BRIEF DESCRIPTION OF THE DRAWINGS

A more complete appreciation of the invention will be obtained by reference to the following Description of the Preferred Embodiments and the accompanying drawings in which like numerals in different figures represent the same structures or elements, wherein:

FIG. 1 shows a sensor according to the invention.

FIG. 2 shows a sectional view of a sensing tip according to the invention.

FIG. 3 shows another sectional view of a sensing tip according to the invention.

FIG. 5. shows the spectrum of low concentration vapor phase trichloroethylene (TCE) taken without the use of the preconcentration tip of the invention.

FIG. 6 shows the spectrum of low concentration vapor phase TCE taken with the use of the preconcentration tip of the invention.

FIG. 7 shows the Raman spectrum of liquid TCE.

DETAILED DESCRIPTION OF THE PREFERRED EMBODIMENTS

Figure 4:
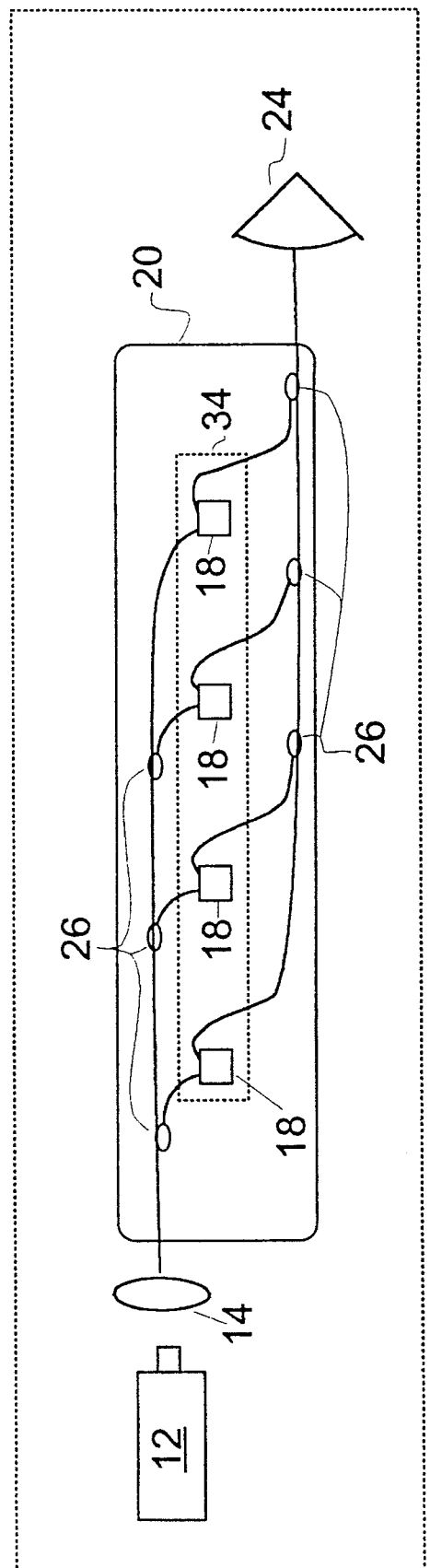
FIG. 4 shows an array according to the invention.

Referring to FIG. 1, a sensor 10 according to the invention uses a laser 12 as a source of Raman excitation radiation. This radiation is directed with conventional focusing optics 14 into an excitation fiber 16. The invention uses a standard detector for Raman radiation 24, which has Raman radiation directed onto it by one or more collection fibers 22.

As described above, and as shown in FIG. 1, the sensor 10 comprises an optical probe 18 optically coupled to a Raman excitation radiation source 12 (typically a laser), typically through an excitation fiber 16, and typically using one or more lenses 14 to direct the excitation radiation into the fiber. The probe is also coupled to a detector of Raman emission 24, typically through one or more collection fibers 22.

In a preferred embodiment of the invention, as shown in FIG. 2, the optical probe 18 includes a jacketing 30 which supports and positions, relative to the adsorbent substrate 32, the terminal end 36 of an excitation fiber 16 disposed to transmit light from the source 12 onto the substrate 32. In a preferred embodiment of the invention, the jacketing 30 supports and positions relative to the substrate 32 the terminal end 38 of the collection fibers 22 disposed to receive Raman emission from the substrate 32 and transmit this light to the detector 24.

In a preferred embodiment, as shown in FIG. 3, the probe 18 comprises the terminal ends 38 of a plurality of collection fibers 22 disposed to transmit light to the detector 24, arranged concentrically about the terminal end of the excitation fiber 16. Preferably, these collection fibers 22 have large diameters, to maximize the amount of collected Raman emission.

Alternatively, referring back to FIG. 1, a single fiber optic waveguide 28 may be used both for transmitting light from the source 12 to the substrate 32 and for transmitting light Raman emission from the substrate 32 to the detector 24. Any of the general methods for combining and separating source and detector beams in a single fiber optic waveguide may be employed in this embodiment of the invention. These methods include using a bifurcated fiber or coupler which joins two fibers into one, using a partially reflecting mirror to split the source and reflected light, and using a spatial filter to separate the source and reflected light. See U.S. Pat. No. 4,792,689, issued Dec. 20, 1988 to Peterson, incorporated by reference herein.

In a preferred embodiment of the invention, the detector 24 comprises a phototransistor, a phototube, a photomultiplier tube, or a CCD. The detector must be sensitive to light in the wavelength band from about 400 nm to about 1100 nm, corresponding to wavelength range of Raman radiation. CCD detectors are particularly preferred, since these rugged detectors provide direct and continuous spectral analysis. Alternatively, the detector may include spectral analysis circuitry, such as Fourier analysis circuitry.

In a preferred embodiment of the invention, the source 12 comprises a laser operating at wavelengths between about 400 nm and about 900 nm. Since scattering is approximately proportional to $1/\lambda^4$, the shorter end of this wavelength scale achieves more scattering. At the longer end of this range, greater intensities are needed to produce the same amount of scattering. The operating wavelength of the source 12 should be selected to avoid fluorescence, since any fluorescence will add to the overall noise level of the detected signal. Typically, the source light is highly monochromatic ($\Delta\lambda \leq 2$ nm). Good results have been achieved with a 488 nm cw Ar laser with a 300 mW output.

The substrate 32 most typically will be a polymer substrate. However, other substrates will be suitable, including silica gel, alumina, and modified silica gel coated with a polymer (such as would be used as a stationary phase for liquid or gas chromatography). In a preferred embodiment of the invention, the polymer substrate 32 comprises a low density, low crystallinity polymer. It is preferred to use a polymer substrate with a high surface area to volume ratio. Powders are particularly preferred. Most preferably, these powders are fine, e.g., having average diameters below 100 μm.

The substrate 32 must reversibly adsorb the organic analyte of interest, according to the equation:

This reaction will have an associated equilibrium constant $K_{eq}$, which preferably will be not less than about 0.25.

In one embodiment of the invention, the polymer substrate 32 is selected for non-preferential adsorption of organic analytes. Preferably, in this embodiment of the invention, a broad range of organic compounds are adsorbed in significant (i.e., measurable) amounts by the substrate. Differences in the adsorption equilibrium constants of different organic species may be accounted for by calibration curves for each analyte species. An example of a polymer useful for this embodiment of the invention is polyethylene.

In another embodiment of the invention, the polymer substrate 32 is selected for preferential adsorption of organic analytes. Preferably, in this embodiment of the invention, the polymer substrate preferentially adsorbs a narrow range of organic compounds (i.e., the equilibrium constant will be much higher for these compounds than for others). More preferably, the polymer substrate preferentially adsorbs a single analyte of interest. Preferably, in this embodiment of the invention, the difference in adsorbtivity between the analyte of interest and the polymer substrate, and the adsorbtivity between other organic compounds and the polymer substrate, is at least an order of magnitude.

As noted supra, a large number of polymers have been identified as selective adsorbents for particular organic analytes. Skilled practitioners will take advantage of this knowledge in practicing this embodiment of the invention. A small sample of available polymer substrates, together with the analytes these substrates preferentially adsorb, are listed in Table I, above.

In a preferred embodiment of the invention, as shown in FIG. 4, an array of probes 18 each comprise a substrate 32. In each of these probes, the terminal end of the excitation fiber is positioned to direct excitation light onto a substrate 32. Raman signals are collected from any analytes adsorbed onto these substrates, and directed to a detector 24. Preferably, each of the substrates in the array comprises a distinct polymer selected for preferential adsorption of a distinct analyte species. Preferably, these probes are coupled through appropriate coupling optics to the source 12 and the detector 24. One particular way of building such an array is shown in FIG. 4. As shown in FIG. 4, light from the excitation source 12 may be divided among a plurality of excitation fibers 16, typically with couplers 26. Each of these excitation fibers 16 will direct light to a probe 18. Raman emission from the substrates 32 in these probes 18 will be collected by collection fibers 22, typically combined, most typically with fiber couplers 26, and directed to the detector 24. In this embodiment of the invention, the signal received by the detector will be an average of the signals from the substrates 32.

Alternatively, signals from each of the plurality of substrates 32 will be transmitted through one or more collection fibers 22 to one of a plurality of detectors 24. Thus, each of the substrates will produce a discrete output. The same result may be achieved by some type of multiplexing, such as time division multiplexing, frequency division multiplexing, and wavelength division multiplexing.

In operation, the sensor typically will be calibrated by measuring the intensity of the Raman emission lines of the polymer substrate, or of the fibers.

It will often be desirable to detect volatile organic compounds (or VOCs) in solution (such as aqueous solution) indirectly, by probing the headspace (i.e., enclosed atmosphere) above the solution. For instance, application of the Raman probe for Naval use preferably has the probe detect and measure VOCs dissolved in water. Such solutions typically will be complex, with several dissolved VOCs. Bilge water, cooling water, effluent water, water for use in other industrial applications, and drinking water are typical of the solutions that may be tested by this invention.

Typically, in the embodiments of the invention described above, the analyte will migrate to the vicinity of the adsorbent substrate, through liquid phase and/or vapor phase, via free convection, forced convection (typically stirring), and/or diffusion. Alternatively, it may be desirable for any of these embodiments of the invention to direct vapor or liquid flow over the substrate to bring the organic analyte into the vicinity of the substrate. For example, the substrate may be disposed in a tube or channel, and liquid or vapor suspected of containing the organic analytes may be directed to flow through this tube and over the substrate, through the use of a pump, gravity, or other means.

Typically, the raman excitation radiation will be directed onto the substrate, and any raman signal will be collected, while the substrate is in situ. However, if a substrate having a sufficiently high binding affinity for the target analyte is selected, it may be possible to expose the substrate to the suspected liquid or vapor, to permit adsorption of any of the organic analyte which may be present. Subsequently, within a time that is short enough for the substrate to retain a significant amount of adsorbed organic analyte, the raman excitation radiation will be directed onto the substrate, and any raman signal will be collected.

Having described the invention, the following examples are given to illustrate specific applications of the invention, including the best mode now known to perform the invention. These specific examples are not intended to limit the scope of the invention described in this application.

In all the examples, the probe comprised one silica excitation fiber surrounded by nine collection fibers. All optical fiber, were about 1 m. in length (this length was chosen for laboratory, convenience; suitable fibers are available at lengths of 500 m. or longer). The Raman probe consisted of one excitation fiber surrounded by 9 collection fibers. All optical fibers were approximately 1 m in length with core/clad diameters of 200/240. A similar configuration has been previously used by McCreery to obtain high quality Raman spectra. See Schwab et al., "Versatile, Efficient Raman Sampling with Fiber Optics", Anal. Chem. 56 (12) pp. 2199–2204 (1984). Approximately 17 mg of low density polyethylene (powder form), contained in a nylon mesh basket, was held on the end of the fiber optic Raman probe. The probe was placed in a large (V=4.360L) glass flask, having a side arm for purging the system. The probe was held by a rubber stopper, which was then placed in the flask. The probe projected down approximately 2 cm into the flask, approximately 1 cm above the sidearm. The low density polyethylene was held close to the ends of the collection and excitation fibers. Laser light from the excitation fiber illuminated the polymer. The nine collection fibers surrounding the excitation fiber collected any light backscattered from the polymer. Excitation light was provided by the 488 nm line of an argon ion laser operated at 500 mW.

At the monochromator, the collection fibers were arranged in a vertical line to efficiently image onto the entrance slit of the monochromator. A Spex model 1404 (0.85 m) double monochromator with a 1200 lines/mm ruled grating and a Gallium Arsenide PMT were used for detection.

Once the probe was in place the flask was purged with nitrogen for 10 minutes. After this initial purge the Raman spectrum of the polymeric matrix was taken, to obtain a background signal. After the background was obtained, the flask inlet and outlet ports were shut off and a precise amount of sample was injected into the flask using an analytical quality micro-pipette. The flask was then sealed and the air inside the flask agitated using a Teflon stir bar on the bottom of the flask. The sample was allowed to vaporize and come to equilibrium over a 30 minute period.

Comparative Example 1

Non-Detection of Trichloroethylene by Standard Raman Spectroscopy

The procedure described above was followed, except that the 17 mg of low density polyethylene (powder form) in a nylon mesh basket was omitted. A 677 mg/L sample of trichloroethylene (TCE) in air was introduced into the flask. The spectrum shown in FIG. 5 was produced. The TCE could not be detected.

EXAMPLE 1

Detection of TCE

The procedure described above was followed, including the 17 mg of low density polyethylene (powder form) in a nylon mesh basket. A 677 mg/L sample of TCE in air was introduced into the flask. The spectrum shown in FIG. 6 was produced. This spectrum compares favorably to the Raman spectrum of liquid TCE shown in FIG. 7. This shows the ability of the invention to detect TCE at concentrations below the LLD for standard Raman spectroscopy.

EXAMPLE 2

Normalization of a concentration versus intensity curve for TCE

Figure 8:
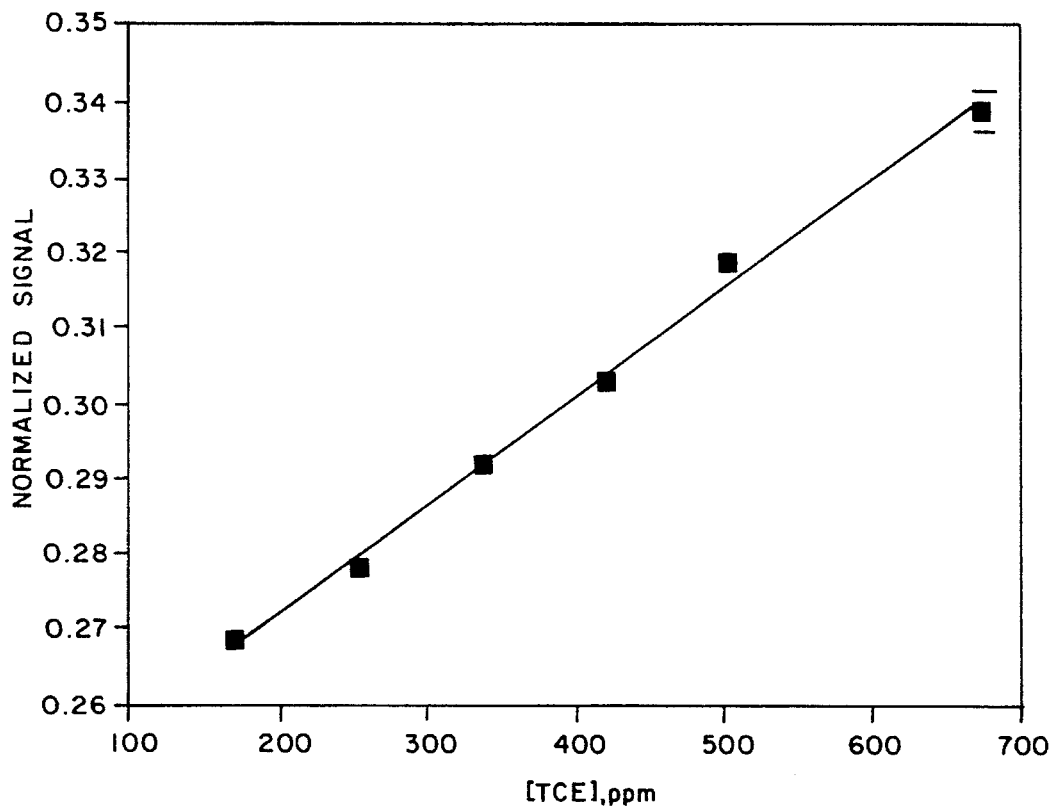
FIG. 8 shows the normalized signal for TCE at varying concentrations.

The procedure from Example 1 was repeated at concentrations of 175, 250, 350, 425, 500, and 677 mg/L. The Raman intensity of the TCE peak at 627.3 $cm^{-1}$ was divided by the Raman intensity of the polymer peak at 1291 $cm^{-1}$, to obtain a normalized intensity. This normalized intensity was plotted against the concentration of TCE vapor, as shown in FIG. 8 (95% confidence interval). Multiple measurements of 670 mg/L TCE vapor using the same probe gave an average value for this ratio of 0.33975±0.0026 (95% confidence interval), with a relative standard deviation of 0.3%. The correlation coefficient of 0.996 indicates a good linear fit for the data.

EXAMPLE 3

Detection of Toluene in a Benzene Background

Figure 9:
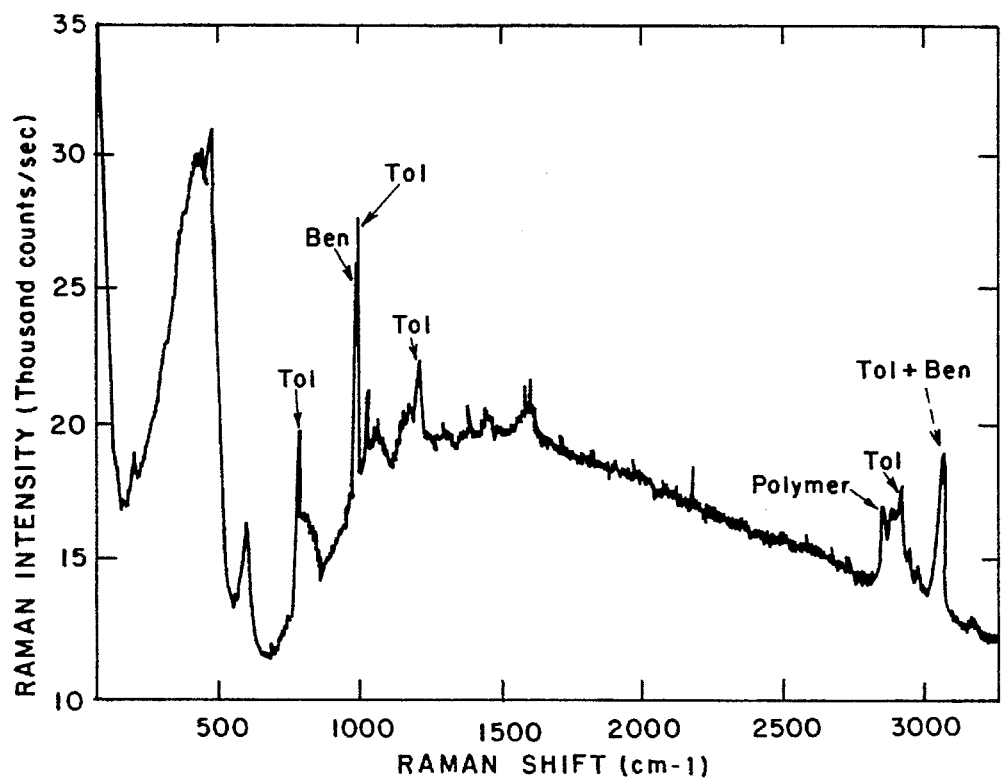
FIG. 9 shows the spectrum of a low concentration benzene/toluene mixture.

The procedure described above was followed, however 25 mg of C-18 (17%) liquid chromatography solid support replaces the low density polyethylene in the nylon mesh basket. A series of samples of toluene were introduced into the flask, against a constant benzene background concentration of 100 mg/L. The LLD for toluene against this benzene background was 4 mg/L. FIG. 9 shows the spectrum of 100 mg/L toluene against a background of 100 m/L benzene. This example shows the high selectivity and sensitivity of the sensor.

EXAMPLE 4

Preparation of a Calibration Curve for Toluene in a Benzene Background

Figure 10:
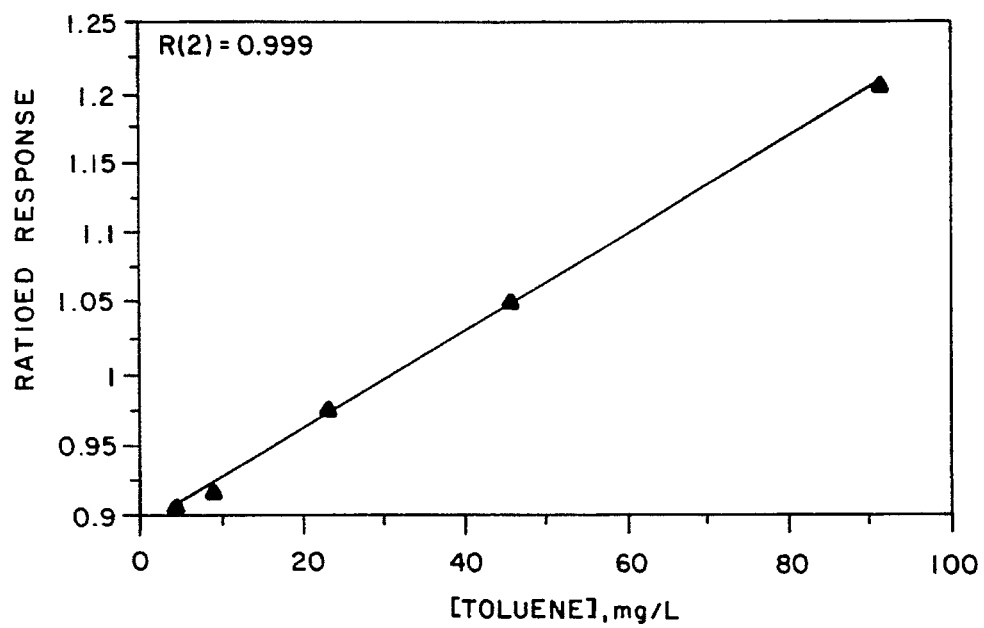
FIG. 10 shows a calibration curve for toluene relative to the silica peaks of the fiber, taken against a benzene background.

The series of samples of toluene in a benzene background described in Example 3 were plotted as in Example 2 (786 $cm^{-1}$ toluene peak). The resulting normalized curve is shown in FIG. 10. This example shows the ability to achieve high linearity even against a background of a related compound.

EXAMPLE 5

Detection of $CCl_4$ in a TCE Background

Figure 11:
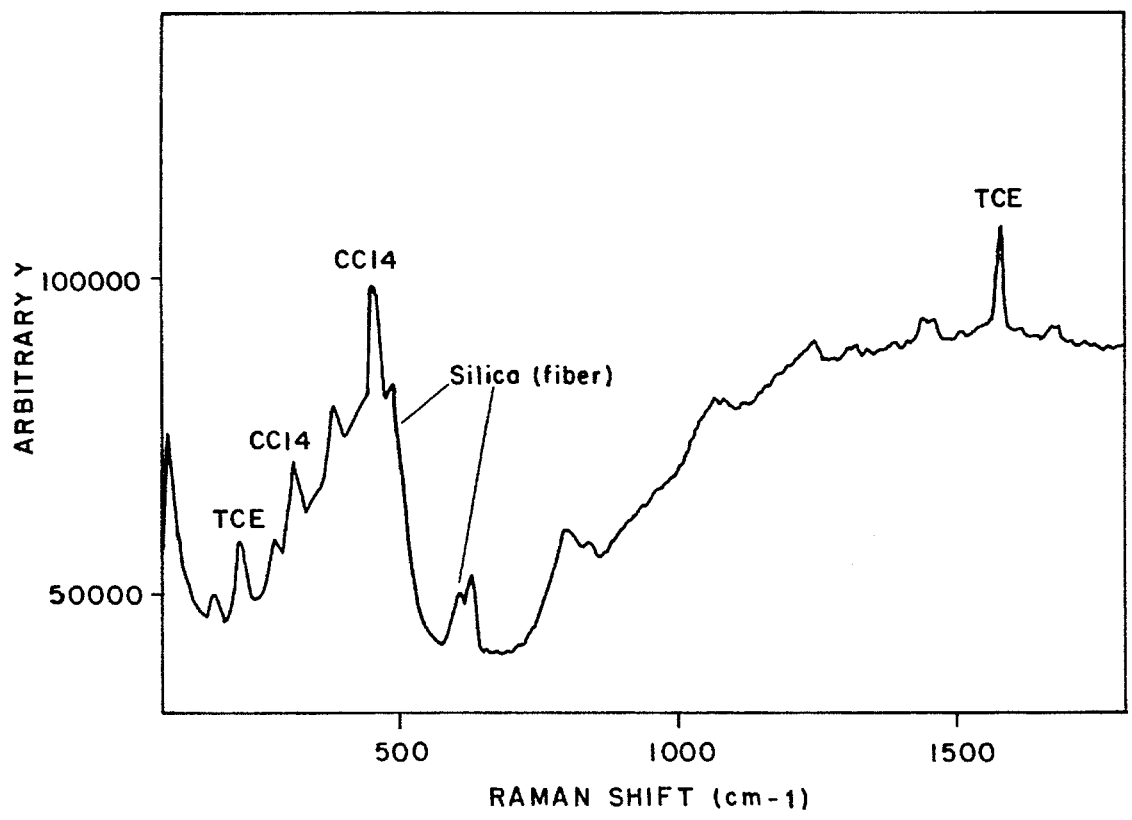
FIG. 11 shows the spectrum of $CCl_4$, taken against a trichloroethylene background.

The procedure described above was followed, including the LC substrate in the nylon mesh basket. A series of samples of $CCl_4$ were introduced into the flask, against a constant TCE background concentration of 500 mg/L. The LLD for $CCl_4$ against this TCE background was 30 mg/L. It is anticipated that using a smaller amount of substrate will enhance the detection limit by having more of the analyte adsorbed by less polymer. FIG. 11 shows the spectrum of 500 mg/L $CCl_4$ against a background of 500 mg/L TCE. This example also shows the high selectivity and sensitivity of the sensor.

EXAMPLE 6

Preparation of a Calibration Curve for $CCl_4$ in a TCE Background

Figure 12:
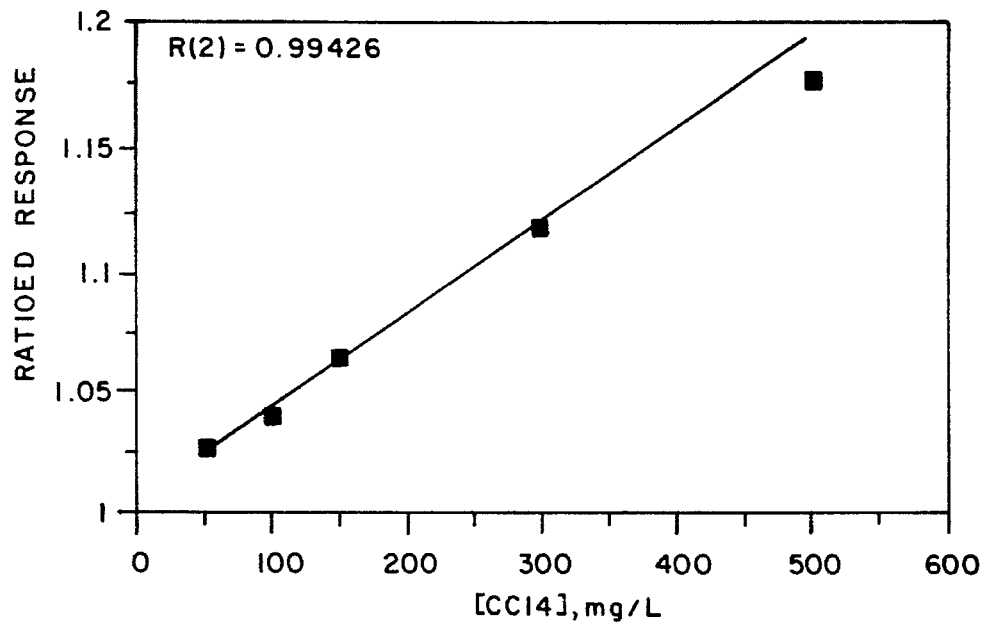
FIG. 12 shows a calibration curve for carbon tetrachloride relative to the silica peaks of the fiber, taken against a trichloroethylene background.

The series of samples of $CCl_4$ in a TCE background described in Example 5 were plotted as in Example 2 (317 $cm^{-1}$ $CCl_4$ peak). The resulting normalized curve is shown in FIG. 12. This example also shows the ability to achieve high linearity against a background of a related compound.

EXAMPLE 7

Detection of Benzene

Figure 13:
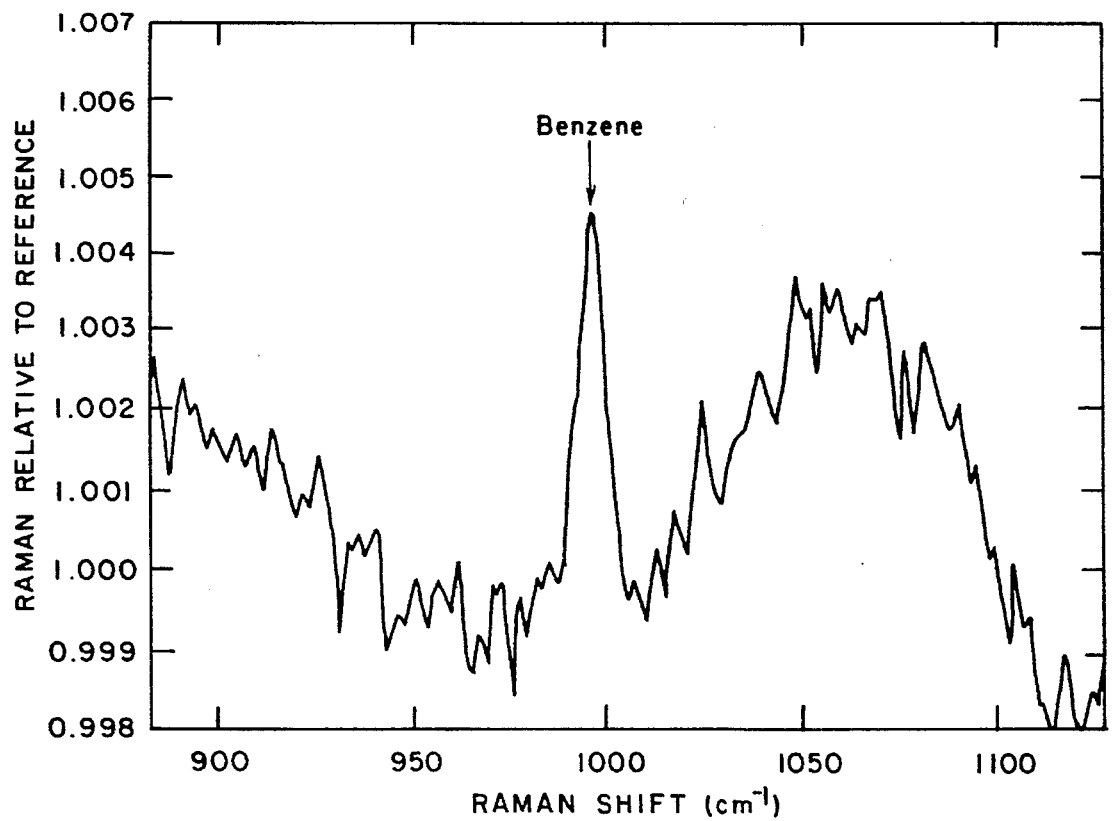
FIG. 13 shows the spectrum of benzene vapor, with the spectrum of the substrate subtracted.

The procedure described above was followed, including the LC substrate in the nylon mesh basket. A 500 ppm sample of benzene was introduced into the flask. The total spectrum was taken, and the predetermined polymer spectrum was subtracted from the total spectrum, using Genplot (a commercially available software package), leaving the spectrum shown in FIG. 13. This example shows a preferred method for improving the sensitivity of the sensor.

EXAMPLE 8

Detection of Volatile Organic Compounds dissolved in Water by Probing the Headspace Over the Liquid The procedure described above was followed, except that the probe was positioned high enough in the flask to be out of the liquid analyte, and in the vapor headspace above the liquid analyte.

A series of aqueous solutions of benzene and toluene were prepared. The concentration of toluene was kept constant at 250 ppm for all samples. The benzene concentration, 250 ppm for the first sample, was lowered stepwise for subsequent samples in 50 ppm decrements to 50 ppm for the last sample.

Headspace measurements were taken by positioning the probe in a sealed flask containing one of these aqueous solutions, and monitoring the signal. The probe was held in the headspace over the stirred solution for 20 minutes.

Raman spectra were acquired at 2, 5, 8, 13, 20, and 30 minutes. Data in Table II indicate that the best results with respect to linearity and detection limits were obtained 8 minutes into the experiment.

TABLE II

| Time, min. | x | b | $R^2$ | Detection Limit, ppm |
|---|---|---|---|---|
| 2 | 1.24 | −12.8 | 0.83 | 75 |
| 5 | 1.71 | 0.66 | 0.98 | 23 |
| 8 | 1.74 | −4.1 | 1.00 | 12 |
| 13 | 1.84 | −12.7 | 0.94 | 41 |
| 20 | 1.67 | −0.14 | 0.99 | 16 |
| 30 | 1.46 | 7.68 | 0.88 | 63 |

Figure 14:
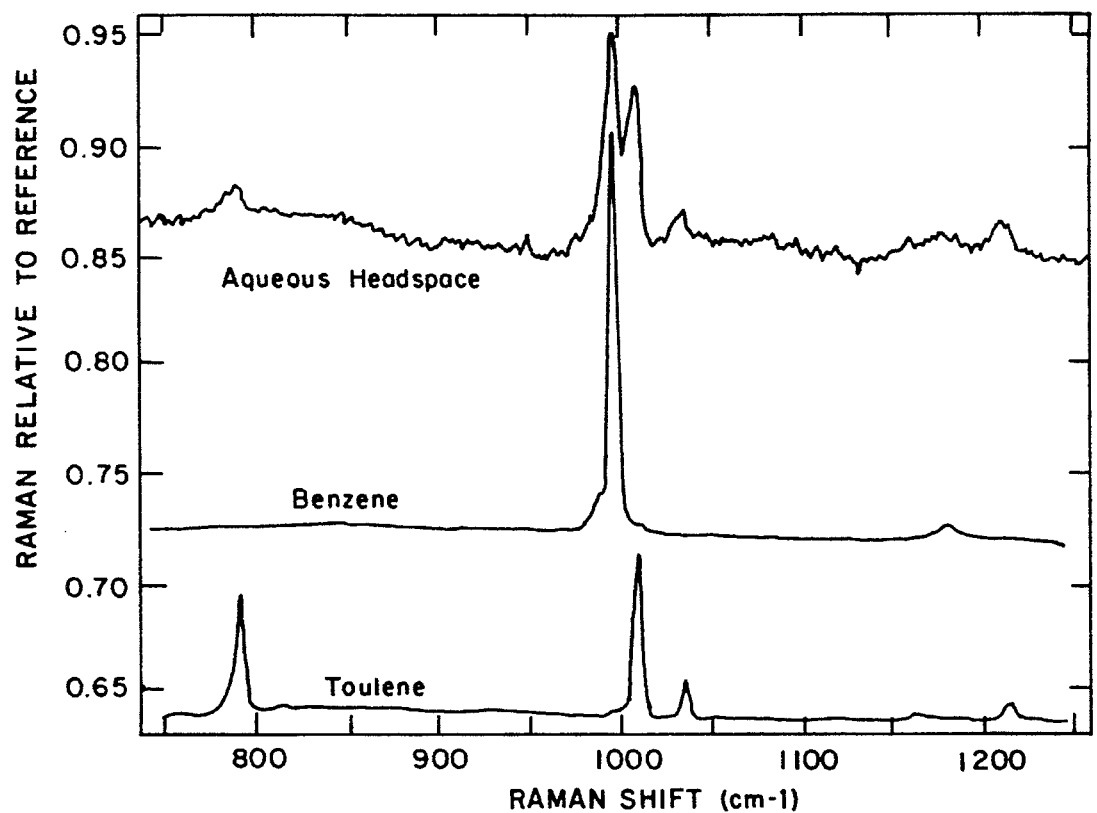
FIG. 14 shows the measured Raman spectrum of the headspace above an aqueous solution containing toluene and benzene, with the Raman spectra of liquid toluene and benzene for comparison.

The measured Raman spectrum of the headspace above an aqueous solution containing 250 ppm toluene and 250 ppm benzene, as well as the Raman spectra of liquid toluene and benzene for the sake of comparison, is shown in FIG. 14.

Figure 15:
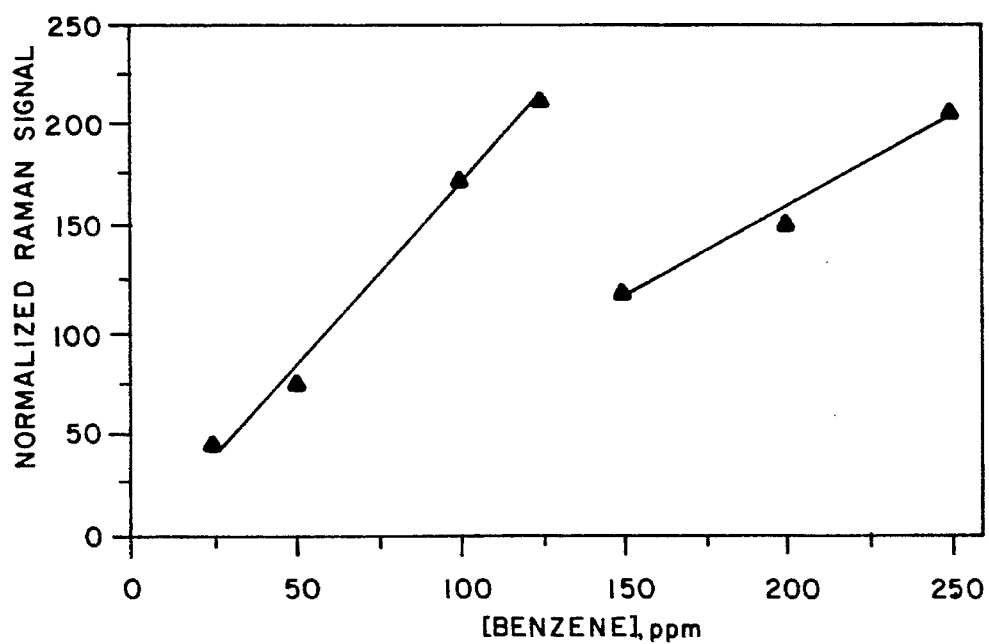
FIG. 15 shows calibration curves for low and high concentrations of benzene in aqueous solution.

The plot of the Raman line intensity for the benzene peak at 986 cm$^{-1}$ versus aqueous benzene concentration is shown in FIG. 15. This plot includes two different lines, one corresponding to low benzene concentrations, and the other corresponding to high benzene concentrations. Two different lines were also observed at the other time intervals. Detection limits at t=8 min. for the low and high concentration curves were calculated to be 12 ppm and 34 ppm, respectively.

Obviously, many modifications and variations of the present invention are possible in light of the above teachings. It is therefore to be understood that, within the scope of the appended claims, the invention may be practiced otherwise than as specifically described.

What is claimed is:

1. An apparatus for detecting an organic compound which generates a raman signal, comprising:
   a non-SERS substrate capable of reversible adsorption of said organic compound;
   a source of raman excitation radiation, positioned for directing said raman excitation radiation onto said non-SERS substrate, for generating a raman signal; and
   a raman signal detector, positioned for detecting said raman signal.

2. The apparatus of claim 1, wherein said substrate comprises a powder.

3. The apparatus of claim 2, wherein said powder has an average diameter of less than 100 μm.

4. The apparatus of claim 1, wherein said substrate is a polymer substrate selected for non-preferential adsorbtion of said organic compound.

5. The apparatus of claim 1, wherein said substrate is a polymer substrate selected for preferential adsorbtion of said organic compound.

6. The apparatus of claim 5, wherein said polymer substrate comprises poly(isobutylene).

7. The apparatus of claim 5, wherein said polymer substrate comprises poly(cyanoallyl)siloxane.

8. The apparatus of claim 5, wherein said polymer substrate comprises poly(phenylether).

9. The apparatus of claim 5, wherein said polymer substrate comprises Fluropolyol.

10. The apparatus of claim 1, wherein said substrate is a polymer substrate having a density less than 2.0 g/cm$^3$.

11. The apparatus of claim 1, wherein said substrate is a polymer substrate having a crystallinity less than 50%.

12. The apparatus of claim 1, wherein said reversible adsorption of said organic compound onto said substrate has an associated equilibrium constant $K_{eq}$ not less than 0.25.

13. The apparatus of claim 1, further comprising optical fiber means for directing said raman excitation radiation onto said substrate.

14. The apparatus of claim 1, further comprising optical fiber means for collecting said raman signal and directing said raman signal to said raman signal detector.

15. The apparatus of claim 1, wherein said substrate comprises silica gel or alumina.

16. The apparatus of claim 1, wherein said substrate comprises silica gel coated with a polymer.

17. The apparatus of claim 1, wherein said substrate is a non-metallic substrate.

18. The apparatus of claim 1, wherein said substrate has a single active layer for reversible adsorption of said organic compound.

19. The apparatus of claim 1, wherein said substrate does not comprise a thin metallic layer for adsorption of said organic compound.

20. An apparatus for detecting a volatile organic compound in a solution, comprising:
    enclosing means for enclosing a headspace above said solution;
    a non-SERS substrate capable of reversible adsorption of vapor of said organic compound, disposed in said headspace;
    a source of raman excitation radiation, positioned for directing said raman excitation radiation onto said non-SERS substrate, for generating a raman signal; and
    a raman signal detector, positioned for detecting said raman signal.

21. A probe for use in detecting an organic compound which generates a raman signal, comprising:
    a non-SERS substrate capable of reversible adsorption of said organic compound;
    optical fiber means for directing raman excitation radiation onto said non-SERS substrate; and
    optical fiber means for collecting a raman signal from said non-SERS substrate and directing said raman signal to a raman signal detector.

* * * * *